United States Patent
Pendergast, Jr. et al.

(10) Patent No.: US 10,626,097 B2
(45) Date of Patent: Apr. 21, 2020

(54) PROCESS FOR MAKING HYDROXYETHYL PIPERAZINE COMPOUNDS

(71) Applicant: Dow Global Technologies LLC, Midland, MI (US)

(72) Inventors: John G. Pendergast, Jr., Pearland, TX (US); Ravindra S. Dixit, Lake Jackson, TX (US); Stephen W. King, League City, TX (US); Christophe R. Laroche, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 186 days.

(21) Appl. No.: 15/743,772

(22) PCT Filed: Jul. 8, 2016

(86) PCT No.: PCT/US2016/041427
§ 371 (c)(1),
(2) Date: Jan. 11, 2018

(87) PCT Pub. No.: WO2017/011283
PCT Pub. Date: Jan. 19, 2017

(65) Prior Publication Data
US 2018/0208567 A1 Jul. 26, 2018

Related U.S. Application Data

(60) Provisional application No. 62/192,778, filed on Jul. 15, 2015.

(51) Int. Cl.
*C07D 295/08* (2006.01)
*C07C 213/04* (2006.01)
*B01D 3/14* (2006.01)
*C07B 63/02* (2006.01)
*C07D 295/088* (2006.01)
*B01D 3/00* (2006.01)

(52) U.S. Cl.
CPC ......... *C07D 295/088* (2013.01); *B01D 3/009* (2013.01); *B01D 3/14* (2013.01); *C07B 63/02* (2013.01); *C07C 213/04* (2013.01); *B01D 2257/70* (2013.01); *Y02P 20/127* (2015.11)

(58) Field of Classification Search
CPC ........ C07D 285/88; B01D 3/14; C07B 63/02; C07C 213/04
USPC .......................................... 544/401; 564/503
See application file for complete search history.

(56) References Cited

U.S. PATENT DOCUMENTS

| 4,435,595 | A | | 3/1984 | Agreda et al. |
|---|---|---|---|---|
| 5,104,987 | A | * | 4/1992 | King ........................ B01J 23/00 544/401 |
| 5,368,691 | A | * | 11/1994 | Asselineau ............ B01D 3/009 203/29 |
| 6,013,801 | A | * | 1/2000 | Koll ........................ C07C 213/04 544/401 |
| 2013/0197266 | A1 | | 8/2013 | Gadewar et al. |
| 2013/0310598 | A1 | | 11/2013 | Terrill et al. |
| 2014/0364655 | A1 | | 12/2014 | Smith |
| 2014/0378771 | A1 | | 12/2014 | St. Onge et al. |

* cited by examiner

Primary Examiner — Venkataraman Balasubramanian

(57) ABSTRACT

The present invention relates to an improved process for making hydroxyethyl piperazine compounds especially mono-hydroxyethyl piperazine. The improvement comprises reacting piperazine and an alkylene oxide, preferably ethylene oxide in a reactive distillation column.

11 Claims, 1 Drawing Sheet

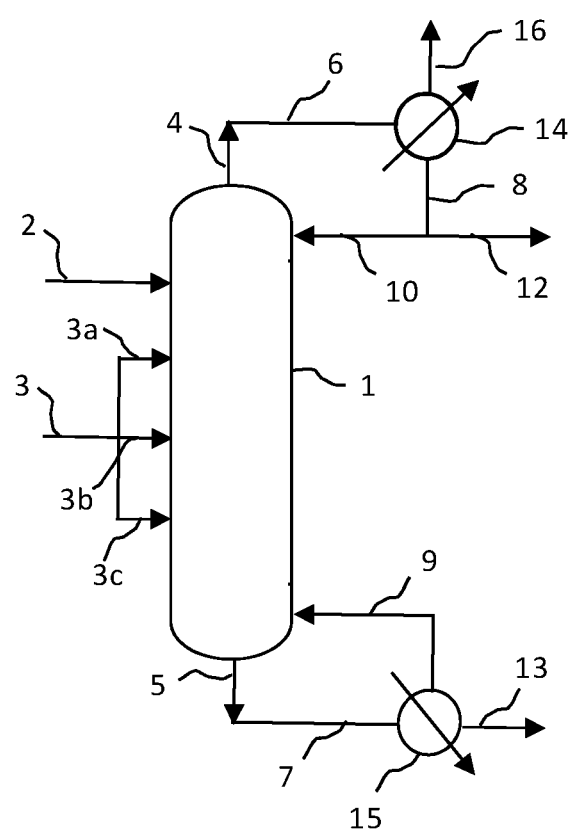

PROCESS FOR MAKING HYDROXYETHYL PIPERAZINE COMPOUNDS

FIELD OF THE INVENTION

The present invention relates to an improved process for making hydroxyethyl piperazine compounds especially mono-hydroxyethyl piperazine. Said process relates to ethoxylation of piperazine with an alkylene oxide, preferably ethylene oxide using reactive distillation to increase the yield of mono-hydroxyethyl piperazine over di-hydroxyethyl piperazine.

BACKGROUND OF THE INVENTION

Hydroxyethyl piperazine compounds are generally made by reacting an excess of ethylene oxide with piperazine. One of the difficulties is that, in addition to producing mono-hydroxyethyl piperazine, the ethoxylation of piperazine leads to the formation of di-hydroxyethyl piperazine as a byproduct along with any unreacted ethylene oxide and/or piperazine. Whether a batch or a continuous process is employed, the resulting reaction mixture must be separated by multistep distillation to isolate the desired hydroxyethyl piperazine compound from the by-products, for example see U.S. Pat. No. 6,013,801.

Reactive distillation is well known, for example see, U.S. Pat. No. 5,368,691, and is generally favored for the case of reacting away an azeotrope and driving a reaction to completion. For example see U.S. Pat. No. 4,435,595 for the production of methyl acetate, US Patent Application No. 2013/0197266 for the production of ethyl acetate, US Patent Application No. 2013/0310598 for the production of glycolate ester oligomers, US Patent Application No. 2014/03787712 for the alkanolysis of polyether polyols to polyester polyols, and US Patent Application No. 2014/0364655 for producing allyl alcohols.

It would be desirable to have a process to make hydroxyethyl piperazine compounds which favors the production of mono-hydroxyethyl piperazine and/or eliminates the need for a separate multistep distillation.

SUMMARY OF THE INVENTION

The present invention is such a process for producing hydroxyalkyl piperazine compounds, preferably hydroxyethyl piperazine compounds, preferably 1-(2-hydroxyethyl) piperazine, 1,4-bis(2-hydroxyethyl)piperazine, and mixtures thereof, comprising the steps of: i) feeding a feed stream of piperazine at a first location into a reactive distillation column having a top, middle, and a bottom, ii) feeding a feed stream of an alkylene oxide, preferably ethylene oxide, at one or more second location into the reactive distillation column, iii) performing the reaction of piperazine and the alkylene oxide, preferably ethylene oxide, in a reaction zone of the reactive distillation column, iv) removing an overhead stream comprising unreacted piperazine from the top of the reactive distillation column, v) removing a bottoms product containing hydroxyethyl piperazine compounds from the bottom of the reactive distillation column.

In one embodiment of the process disclosed herein above, the first location of the feed stream of piperazine is towards the top of the reactive distillation column and the second location of the feed stream of the alkylene oxide, preferably ethylene oxide, is at a location lower on the reactive distillation column than the first location.

In one embodiment of the processes disclosed herein above, the alkylene oxide, preferably ethylene oxide, feed is fed at multiple locations into the reactive distillation column.

In another embodiment, the processes disclosed herein above further comprises the steps of: vi) passing the removed overhead stream comprising unreacted piperazine through a condenser, vii) condensing the unreacted piperazine from the overhead stream, and viii) recycling the unreacted piperazine back into the reactive distillation column at a third location which is above the second location of the alkylene oxide, preferably ethylene oxide, feed.

In another embodiment, the processes disclosed herein above further comprise the steps of: ix) passing at least a portion of the bottoms product through a reboiler, x) evaporating a portion of the bottoms product, and xi) adding the evaporated portion back to the bottom of the reactive distillation column.

In one embodiment of the processes disclosed herein above, no catalyst is disposed within the reactive distillation column.

In one embodiment of the processes disclosed herein above, one or more catalyst is disposed within the reactive distillation column.

In one embodiment of the processes disclosed herein above, the pressure in the reactive distillation column is equal to or greater than atmospheric pressure.

In one embodiment of the processes disclosed herein above, the reactive distillation column comprises one or more stage.

In one embodiment of the processes disclosed herein above, the preferred temperatures of the top, middle, and bottom of the reactive distillation column are: top: 140° C. to 160° C., middle: 160° C. to 200° C., and bottom: 200° C. to 250° C.

BRIEF DESCRIPTION OF THE DRAWINGS

FIG. 1 shows a two feed system for producing hydroxyethyl piperazine compounds according to the present invention using a reactive distillation column.

DETAILED DESCRIPTION OF THE INVENTION

The object of the present invention is to produce hydroxyalkyl piperazine compounds, preferably hydroxyethyl piperazine compounds, more preferably mono-hydroxyethyl-piperazine, i.e., 1-(2-hydroxyethyl)piperazine, in such a manner as to simplify the purification process. A further objective of the present invention is to improve the yield of mono-hydroxyethyl-piperazine as compared to the amount of di-hydroxyethyl-piperazine, e.g., 1,4-bis(2-hydroxyethyl) piperazine and other by products. Another object of the present invention is that the reaction may be carried out continuously so as to avoid the problems associated with a reaction carried out batchwise.

It has now been found that these objectives are reached by reacting an alkylene oxide, for example a $C_2$ to $C_8$ alkylene oxide, preferably propylene oxide, more preferably ethylene oxide and piperazine in a reactive distillation process.

In chemical processing, chemical reaction and the purification of the desired products by distillation may be carried out sequentially. The performance of this chemical process structure may be improved by the integration of reaction and distillation in a single multifunctional process unit. This integration concept is called "reactive distillation." As advantages of this integration, chemical equilibrium limitations may be overcome, higher selectivities may be achieved, the heat of reaction may be used in situ for distillation, auxiliary solvents may be avoided, and/or azeotropic and/or closely boiling mixtures may be more easily separated. Increased process efficiency and reduction in overall capital costs may result from the use of this approach.

A reactive distillation system comprises at least one separator (e.g., a distillation column) comprising a top, middle, and bottom in which the separator, or column, comprises a reaction zone in which a reaction is occurring. In general, suitable separators may include any process equipment suitable for separating at least one inlet stream into a plurality of effluent streams having different compositions, states, temperatures, and/or pressures. For example, the separator may be a column with, or without, a plurality of stages, i.e., trays, packing, or some other type of complex internal structure. Examples of such columns include scrubbers, strippers, absorbers, adsorbers, packed columns, and distillation columns having valve, sieve, or other types of trays. Such columns may employ weirs, downspouts, internal baffles, temperature control elements, and/or pressure control elements. Such columns may also employ some combination of reflux condensers and/or reboilers, including intermediate stage condensers and reboilers. In an embodiment, the reactive distillation system described herein may comprise a distillation tower without any catalyst disposed therein. In another embodiment, the reactive distillation system described herein may comprise a distillation column having at least one catalyst disposed therein.

In one embodiment of the invention, the reactive distillation column has two feeds. Piperazine is fed at a first location which is located towards the upper (or top) part of the column and ethylene oxide is fed at one or more second location which is located towards the lower (or bottom) part of the column. A schematic for a double feed reactive distillation column of the process of the present invention is schematically illustrated in FIG. 1. This system includes a reactive distillation column 1 having a reactive zone, a condenser 14, and a reboiler 15. In the illustrated system, the piperazine feed 2 is delivered at or near the top of the reactive distillation column 1, and the ethylene oxide feed 3 is delivered below the piperazine feed 2 at multiple locations, for example 3a, and/or 3b, and/or 3c. Due to boiling point differences of the piperazine and the ethylene oxide, the piperazine moves towards the bottom of the reactive distillation column 1 and the ethylene oxide moves towards the top of the reactive distillation column 1 providing counter current contact between the two. Unreacted piperazine and/or ethylene oxide may move upward exiting the top 4 of the reactive distillation column 1 and the piperazine may be condensed in the condenser 14 for recycle 10 and/or reclamation 12 and ethylene oxide reclaimed or recycled 16. The hydroxyethyl piperazine reaction product, or bottoms product, moves downward exiting the bottom 5 of the reactive distillation column 1 and is obtained as products 13 from the reboiler 15.

Distillate removed at the top of the reactive distillation column 1 is passed through a condenser 14, and ethylene oxide is separated from lower boiling constituents, i.e., piperazine. The ethylene oxide may leave the system as an overhead product stream 16. The condensed lower boiling constituents, or at least some portion thereof, can be cycled back 10 to the reactive distillation column 1 for further reaction and/or separation.

The bottoms product, or portion thereof, may be passed through reboiler 15, where a portion of the bottoms product is evaporated and added back to the bottom of the reactive distillation column 1. The remaining bottoms product may pass out of the system as product stream 13. The product stream 13 comprises the mono-hydroxyethyl piperazine produced in the reactive distillation column 1 along with any side products, i.e., di-hydroxyethyl piperazine, etc., produced by the reaction. The reactive distillation column reflux and reboil ratios are maintained to optimize the amount of mono-hydroxyethyl piperazine in the bottoms product. In an embodiment, the bottoms product stream 13 may comprise greater than 50%, greater than 60%, greater than 70%, greater than 80%, greater than 85%, greater than 90%, or greater than 95% mono-hydroxyethyl piperazine by weight.

In one embodiment, the piperazine recycle 10 is fed into the reactive distillation column at a third location which is above the second location of the piperazine feed 2.

In one embodiment, the piperazine recycle 10 is fed into the reactive distillation column at a third location which is the same level, e.g., stage, as the first location of the piperazine feed 2.

In one embodiment, the piperazine recycle 10 is fed into the reactive distillation column at a third location which is below the first location of the piperazine feed 2 but higher than the second location of the ethylene oxide feed 3.

The reactive distillation column 1 of the process of the present invention may comprise one or more stage. The number of stages is not particularly limited as long as a distillate with unreacted piperazine and ethylene oxide and a bottoms product comprising hydroxyethyl piperazine compounds is produced. Preferably there is one or more stage, more preferably 2 or more stages, more preferably 3 or more stages, and even more preferably 4 or more stages. Preferably there are 30 or less stages, more preferably 20 or less stages, more preferably 15 or less stages, and even more preferably 10 or less stages.

In one embodiment of the process of the present invention, the reactive distillation column does not have any catalyst disposed therein, in other words there is no catalyst disposed within the reactive distillation column.

In one embodiment of the process of the present invention, the reactive distillation column does have one or more catalyst disposed therein, in other words there is one or more catalyst disposed within the reactive distillation column. When a catalyst is present, any suitable ethoxylation catalyst may be used which is known to one skilled in the art. The catalyst may be homogeneous or heterogeneous. A preferred catalyst is a heterogeneous catalyst, for example water, ion exchange resins, zeolites, clays, mixed metal oxides and other solid ethoxylation catalysts known to one skilled in the art.

In one embodiment of the process of the present invention, the reactive distillation column 1 is operated at equal to or greater than atmospheric pressure.

In another embodiment of the process of the present invention, the reactive distillation column 1 is operated at a positive pressure, preferably 1.05 bar absolute, more preferably 1.1 bar absolute, and even more preferably 1.2 bar absolute.

In one embodiment of the process of the present invention, the molar ratio of piperazine feed to ethylene oxide feed is 4 to 1, preferably 3 to 1, preferably 2 to 1, and more preferably 1 to 1.

In one embodiment, the preferred temperatures of the top, middle, and bottom of the reactive distillation column are: top: 140° C. to 160° C., middle: 160° C. to 200° C., and bottom: 200° C. to 250° C.

Preferably, the condenser temperature is from 110° C. to 145° C., more preferably 120° C. to 130° C., and even more preferably 125° C. to 130° C.

EXAMPLE

The process of the present invention is simulated numerically using commercially available software, ASPEN-PLUS™ version 8.6. Physical properties are developed from data regression. The process is numerically simulated by using the rigorous distillation module named RADFRAC within Aspen. This block accommodates both rigorous separation as well as the ability to specify reactions on stages within the tower. These reactions may either be equilibrium reactions or kinetically controlled reactions, as is the case in this application.

A distillation tower provides a means for stage-wise countercurrent contact of liquid proceeding down the tower, with vapor rising up through the device, with the vapor and liquid being brought into intimate contact with the liquid. This may be done with either trays or packing, though in this case, trays are used in the simulation. The absolute units used in this simulation do not necessarily reflect any commercial reality, but rather reflect a demonstration for the concept and practicality of the concept.

The simulation uses a process configuration as shown in FIG. 1 and is a representation of the RADFRAC block with piperazine feed provided to the upper section of the tower. Ethylene oxide, shown coming from a common source and then separated into multiple stream, is fed to stages between the piperazine feed and the bottom of the tower.

Table 1 is a stream table for the process described in FIG. 1. In the illustrative embodiment, a 10 stage unit is configured. Stage 1 is the condenser and Stage 10 is the reboiler. Piperazine (PIP) is introduced above stage 5. Ethylene oxide (EO) is introduced below stages 5, 7 and 9. Piperazine is introduced at or near the top of the column and EO is introduced at or near the bottom of the column. The EO is distributed to lower its concentration to optimize the amount of 1-(2-hydroxyethyl)piperazine (HEP) formed over 1,4-bis(2-hydroxyethyl)piperazine (DIHEP).

TABLE 1

|  | PIP-FEED | EO-TOP | EO-MID | EO-BOT | TOP-PROD | BOT-PROD |
|---|---|---|---|---|---|---|
| Mole Flow kmol/hr | | | | | | |
| PIP | 6.965657 | 0 | 0 | 0 | 2.320443 | 0.7814593 |
| HEP | 0 | 0 | 0 | 0 | 0.000195303 | 3.189589 |
| EO | 0 | 2.594268 | 1.945701 | 0 | 0.00224344 | 3.59E−09 |
| DIHEP | 0 | 0 | 0 | 0 | 3.65E−08 | 0.673971 |
| Mole Frac | | | | | | |
| PIP | 1 | 0 | 0 | 0 | 0.9989501 | 0.168236 |
| HEP | 0 | 0 | 0 | 0 | 8.41E−05 | 0.6866686 |
| EO | 0 | 1 | 1 | 0 | 0.000965798 | 7.72E−10 |
| DIHEP | 0 | 0 | 0 | 0 | 1.57E−08 | 0.1450954 |
| Mass Flow kg/hr | | | | | | |
| PIP | 600 | 0 | 0 | 0 | 199.8757 | 67.31247 |
| HEP | 0 | 0 | 0 | 0 | 0.0254264 | 415.2527 |
| EO | 0 | 114.2857 | 85.71429 | 0 | 0.0988303 | 1.58E−07 |
| DIHEP | 0 | 0 | 0 | 0 | 6.37E−06 | 117.4349 |
| Mass Frac | | | | | | |
| PIP | 1 | 0 | 0 | 0 | 0.9993787 | 0.1121874 |
| HEP | 0 | 0 | 0 | 0 | 0.000127132 | 0.6920878 |
| EO | 0 | 1 | 1 | 0 | 0.000494152 | 2.63E−10 |
| DIHEP | 0 | 0 | 0 | 0 | 3.18E−08 | 0.1957248 |
| Total Flow kmol/hr | 6.965657 | 2.594268 | 1.945701 | 0 | 2.322882 | 4.645019 |
| Total Flow kg/hr | 600 | 114.2857 | 85.71429 | 0 | 200 | 600 |
| Total Flow cum/hr | 0.662639 | 0.1315219 | 0.0986414 | 0 | 0.2335851 | 0.6788775 |
| Temperature ° C. | 100 | 20 | 20 | | 147.7994 | 212.3477 |

Table 2 shows the result of the reactive distillation by stage in units of kilogram moles per hour. The reactants, PIP and EO are shown as being formed, illustrated by the negative numbers. The products, HEP and DIHEP are shown as being formed by the reaction as the PIP is distributed throughout the tower, and the EO proceeds upward through the tower.

TABLE 2

| Stage | PIP | EO | HEP | DIHEP |
|---|---|---|---|---|
| 1 | 0 | 0 | 0 | 0 |
| 2 | −0.07847 | −0.07898 | 0.07796 | 0.00051 |
| 3 | −0.17904 | −0.18282 | 0.175263 | 0.003777 |
| 4 | −0.57152 | −0.60335 | 0.539694 | 0.031827 |
| 5 | −1.59848 | −1.8574 | 1.339548 | 0.258928 |
| 6 | −0.35293 | −0.42151 | 0.284341 | 0.068584 |
| 7 | −1.07262 | −1.37917 | 0.76608 | 0.306543 |
| 8 | −0.01064 | −0.01435 | 0.006919 | 0.003718 |
| 9 | −6.39E−05 | −0.00015 | −2.12E−05 | 8.50E−05 |
| 10 | 0 | 0 | 0 | 0 |

What is claimed is:
1. A process for producing hydroxyalkyl piperazine compounds, comprising the steps of:

i) feeding a feed stream of piperazine at a first location into a reactive distillation column having a top, middle, and a bottom,
ii) feeding a feed stream of ethylene oxide at one or more second location into the reactive distillation column,
iii) performing the reaction of piperazine and ethylene oxide in a reaction zone of the reactive distillation column,
iv) removing an overhead stream comprising unreacted piperazine from the top of the reactive distillation column,
v) removing a bottoms product containing hydroxyethyl piperazine compounds from the bottom of the reactive distillation column, wherein:
the first location of the feed stream of piperazine is towards the top of the reactive distillation column and the second location of the feed stream of ethylene oxide is at a location lower on the reactive distillation column than the first location, and
the ethylene oxide feed is fed at multiple locations into the reactive distillation column.

2. The process of claim 1 further comprising the steps of:
vi) passing the removed overhead stream comprising unreacted piperazine through a condenser,
vii) condensing the unreacted piperazine from the overhead stream,
and
viii) recycling the unreacted piperazine back into the reactive distillation column at a third location which is above the second location of the alkylene oxide feed.

3. The process of claim 1 further comprising the steps of:
ix) passing at least a portion of the bottoms product through a reboiler,
x) evaporating a portion of the bottoms product, and
xi) adding the evaporated portion back to the bottom of the reactive distillation column.

4. The process of any of the preceding claims wherein the hydroxyalkyl piperazine compounds are hydroxyethyl piperazine compounds and the alkylene oxide is ethylene oxide.

5. The process of claim 1 wherein no catalyst is disposed within the reactive distillation column.

6. The process of claim 1 wherein one or more catalyst is disposed within the reactive distillation column.

7. The process of claim 6 wherein the one or more catalyst is selected from water, an ion exchange resin, a zeolite, clay, and mixed metal oxides.

8. The process of claim 1 wherein the pressure in the reactive distillation column is equal to or greater than atmospheric pressure.

9. The process of claim 1 wherein the reactive distillation column comprises one or more stage.

10. The process of claim 1 wherein the temperatures of the top, middle, and bottom of the reactive distillation column are: top: 140° C. to 160° C., middle: 160° C. to 200° C., and bottom: 200° C. to 250° C.

11. The process of claim 4 wherein the hydroxyethyl piperazine compounds comprise 1-(2-hydroxyethyl)piperazine (HEP), 1,4-bis(2-hydroxyethyl)piperazine (DIHEP), or mixtures thereof.

* * * * *